(12) United States Patent
Heilmann et al.

(10) Patent No.: US 11,400,197 B2
(45) Date of Patent: Aug. 2, 2022

(54) DEVICES FOR PERCUTANEOUS PA-LA CANNULATION AND METHODS OF DELIVERING AND USING THE SAME

(71) Applicant: ReCO2very Therapies GMBH, Bad Klosterlausnitz (DE)

(72) Inventors: Torsten Heilmann, Berlin (DE); Sabine Post, Berlin (DE)

(73) Assignee: RECO2VERY THERAPIES GMBH

( * ) Notice: Subject to any disclaimer, the term of this patent is extended or adjusted under 35 U.S.C. 154(b) by 326 days.

(21) Appl. No.: 16/097,147

(22) PCT Filed: Apr. 27, 2017

(86) PCT No.: PCT/EP2017/060018
§ 371 (c)(1),
(2) Date: Oct. 26, 2018

(87) PCT Pub. No.: WO2017/186831
PCT Pub. Date: Nov. 2, 2017

(65) Prior Publication Data
US 2021/0220542 A1     Jul. 22, 2021

(30) Foreign Application Priority Data
Apr. 27, 2016    (EP) .................................. 16167330

(51) Int. Cl.
*A61M 1/36*      (2006.01)
*A61M 1/26*      (2006.01)
*A61M 1/16*      (2006.01)

(52) U.S. Cl.
CPC ........ *A61M 1/3659* (2014.02); *A61M 1/1698* (2013.01); *A61M 1/267* (2014.02);
(Continued)

(58) Field of Classification Search
CPC ...... A61M 1/1698; A61M 1/267; A61M 1/32; A61M 1/3638; A61M 1/3653;
(Continued)

(56) References Cited

U.S. PATENT DOCUMENTS 10,434,238 B2 * 10/2019 Pesenti ............... A61M 1/3482
2002/0128586 A1 * 9/2002 Barbut ................ A61M 1/3653
                                                          604/6.14
(Continued)

FOREIGN PATENT DOCUMENTS

WO     2009/051967 A1    4/2009
WO     2013/026148 A1    2/2013
(Continued)

OTHER PUBLICATIONS

International Search Report and Written Opinion for PCT/EP2017/060018, dated Jul. 21, 2017.
(Continued)

*Primary Examiner* — Benjamin J Klein
(74) *Attorney, Agent, or Firm* — McDonnell Boehnen Hulbert & Berghoff LLP

(57) ABSTRACT

A pulmonary artery (PA) via trans-septal to left atrial (LA) percutaneous dual lumen cannulation system which reduce the pressure of the right ventricle provides drainage of pulmonary artery blood with bypassing the lung while return the blood to the Left Atrium (LA) without the need for thoracotomy for a wearable pump less extra corporeal lung assist (pECLA) to remove $CO_2$, pump less extra corporeal membrane oxygenation (ECMO), para-corporeal pump driven $CO_2$ removal, extra corporeal $CO_2$ removal ($ECCO_2R$) pump driven, para-corporeal pump driven membrane oxygenation, or extra corporeal membrane oxygenation (ECMO) with extra-corporeal pump. By establishing percutaneously a shunt with a dual lumen cannula between (Continued)

PA and LA using the PA-LA pressure gradient as the driving force for the blood flow through the drainage lumen, $CO_2$ removal device, or oxygenator and return cannula lumen in the vascular system.

23 Claims, 10 Drawing Sheets

(52) U.S. Cl.
CPC ... *A61M 1/3638* (2014.02); *A61M 2205/3331* (2013.01); *A61M 2205/3334* (2013.01)

(58) Field of Classification Search
CPC .............. A61M 1/3659; A61M 1/3666; A61M 2202/0225; A61M 2205/3331; A61M 2205/3334
See application file for complete search history.

(56) References Cited

U.S. PATENT DOCUMENTS

| | | | |
|---|---|---|---|
| 2005/0059925 A1* | 3/2005 | Maginot | A61M 25/0194 604/43 |
| 2011/0130619 A1* | 6/2011 | Whisenant | A61M 60/135 600/16 |
| 2014/0255253 A1* | 9/2014 | Fusch | A61M 1/1698 422/48 |
| 2015/0335801 A1* | 11/2015 | Farnan | A61M 60/178 600/16 |
| 2016/0008531 A1* | 1/2016 | Wang | A61M 1/3666 600/16 |
| 2016/0008573 A1* | 1/2016 | Loesener | A61M 25/0102 604/510 |
| 2016/0114124 A1* | 4/2016 | Tal | A61M 1/285 604/43 |

FOREIGN PATENT DOCUMENTS

| | | |
|---|---|---|
| WO | 2014/197614 A1 | 12/2014 |
| WO | 2016/011091 A1 | 1/2016 |
| WO | 2016/016870 A1 | 2/2016 |

OTHER PUBLICATIONS

Garcia, et al., "Ambulatory extracorporeal membrane oxygenation: A new approach for bridge-to-lung transplantation,"Journal of Thoracic and Cardiovascular Surgery, Mosby-Year Book, Inc., St. Louis, MO, US, vol. 139, No. 6, Jun. 1, 2010 (Jun. 1, 2010), pp. e137-e139.

Camporota, et al., (2016) "Current Applications for the Use of Extracorporeal Carbon Dioxide Removal in Critically Ill Patients," BioMed Research International vol. 2016, Article ID 9781695, 8 pages.

Slutsky, et al., (2013), "Ventilator-Induced Lung Injury," N Engl J Med 2013;369:2126-36.

Morimont, et al., "Update on the role of extracorporeal CO2 removal as an adjunct to mechanical ventilation in ARDS," Critical Care (2015) 19:117.

Benza, et al., "Predicting Survival in Pulmonary Arterial Hypertension," Circulation, (2010) 122:164-172.

Dandel, et al., "Survival of Patients With Idiopathic Pulmonary Arterial Hypertension After Listing for Transplantation: Impact of Iloprost and Bosentan Treatment," J Heart Lung Transplant 2007;26:898-906.

Chen, et al. "Impact of the Lung Allocation Score on Lung Transplantation for Pulmonary Arterial Hypertension," Am J Respir Crit Care Med vol. 180. pp 468-474, 2009.

Mangi, et al., "Bridge to lung transplantation using short-term ambulatory extracorporeal membrane oxygenation," J Thorac Cardiovasc Surg 2010;140:713-5.

Garcia, et al. "Ambulatory extracorporeal membrane oxygenation: A new approach for bridge-to-lung transplantation," J Thorac Cardiovasc Surg 2010;139:e137-9.

Fadel, et al., "Long-term outcome of double-lung and heart-lung transplantation for pulmonary hypertension: a comparative retrospective study of 219 patients," European Journal of Cardiothoracic Surgery, 38 (2010) 277-284.

Fischer, et al., "Bridge to Lung Transplantation With the Extracorporeal Membrane Ventilator Novalung in the Veno-Venous Mode: The Initial Hannover Experience," ASAIO Journal 2007; 53:168-170.

Hoeper and Welte, "Extracorporeal lung assist: more than kicking a dead horse?," Eur Respir J 2008; 32: 1431-1432.

Fischer, et al., "Bridge to lung transplantation with the novel pumpless interventional lung assist device NovaLung," J Thorac Cardiovasc Surg 2006;131:719-23.

Strueber, et al., "Bridge to Thoracic Organ Transplantation in Patients with Pulmonary Arterial Hypertension Using a Pumpless Lung Assist Device," American Journal of Transplantation 2009; 9: 853-857.

Schmid, et al., "Bridge to Lung Transplantation Through a Pulmonary Artery to Left Atrial Oxygenator Circuit," Ann Thorac Surg 2008;85:1202-5.

* cited by examiner

DEVICES FOR PERCUTANEOUS PA-LA CANNULATION AND METHODS OF DELIVERING AND USING THE SAME

This application is a U.S. national phase application under 35 USC 371 of International Patent Application no. PCT/EP2017/060018, filed Apr. 27, 2017, which claims the benefit of European Application no. 16167330.6, filed Apr. 27, 2016.

The invention relates to a multi or dual lumen cannulation assembly. The assembly may be configured for percutaneously placing tubes into the pulmonary artery (PA) and/or trans-septally via or in the left atrium (LA) to reduce the pressure of the right ventricle, to provide drainage of pulmonary artery blood with bypassing the lung and returning the blood to the heart, e.g. the LA, without the need for thoracotomy. The invention further relates to an assembly or system comprising such multi or dual lumen cannula. The assembly or system may further comprise a wearable pump less extra corporeal lung assist (pECLA) to remove $CO_2$, which may further comprise pump less extra corporeal membrane oxygenation (ECMO), para-corporeal pump driven $CO_2$ removal, extra corporeal $CO_2$ removal ($ECCO_2R$) pump driven, para-corporeal pump driven membrane oxygenation, or extra corporeal membrane oxygenation (ECMO) with extra-corporeal pump. The invention further relates to methods of applying such assemblies in methods of treating patients with lung and/or heart diseases or to methods of treating patients with lung and/or heart diseases.

BACKGROUND OF THE INVENTION

Respiratory failure—a condition in which the respiratory system is unable to maintain adequate gas exchange to satisfy metabolic demands—is the most common cause of admission to critical care, and because of the increase of life expectancy in industrialized countries, respiratory diseases will represent the third most common cause of death by 2025. An important syndrome leading to respiratory failure in critically ill patients is the acute respiratory distress syndrome (ARDS), which leads to poor lung function with hypoxaemia, hypercapnia, and low respiratory system compliance (see L. Camporota and N. Barrett, "Current Application for the Use of Extracorporeal Carbon Dioxide Removal in Critically Ill Patients," *BioMed Research International*, 2016, Vol. 2016, p. 8).

In these conditions, mechanical ventilation is often able to provide adequate oxygenation and $CO_2$ removal. However, the improvement of gas exchange commonly occurs at the expense of a secondary injury to the lung (ventilator-induced lung injury or VILI) due to inhomogeneous lung overdistension. VILI can lead to the release of inflammatory mediators that reach other organs causing multiple organ failure (see A. S. Slutsky and V. M. Ranieri, "Ventilator-induced lung injury," *The New England Journal of Medicine*, 2013, Vol. 369, No. 22, pp. 2126-2136).

Ultra-protective ventilation strategies are likely to lead to hypercapnia and its deleterious consequences including systemic and cerebral vasodilatation, cardiovascular depression, arrhythmia, and pulmonary vasoconstriction with an increase in pulmonary arterial pressure. Acute pulmonary hypertension increases right ventricle (RV) afterload and causes acute cor pulmonale which is associated with high mortality rates (see P. Morimont, et al., "Update on the role of extracorporeal $CO_2$ removal as an adjunct to mechanical ventilation in ARDS," *Critical Care*, 2015, Vol. 19, No. 1).

The need to correct hypercapnia without exposing the lung to mechanical trauma has resulted in a renewed interest in extracorporeal technologies that facilitate extracorporeal $CO_2$ removal ($ECCO_2R$).

$ECCO_2R$ is a technique of partial respiratory support that achieves removal of $CO_2$ from the blood through a low blood flow (0.4-1 L/min) extracorporeal circuit, without significant effect on blood oxygenation. This is in comparison to extracorporeal membrane oxygenation which uses blood flows of 3-7 L/min to provide total respiratory support with significant oxygenation and $CO_2$ removal.

The survival of patients with idiopathic pulmonary arterial hypertension (iPAH) has improved during the past 15 years with the development of specific medical therapy. However, many patients continue to deteriorate despite maximal therapy, and lung transplantation remains the only therapeutic option for patients with advanced iPAH (see Benza R L, et al. "Predicting survival in pulmonary arterial hypertension: insights from the Registry to Evaluate Early and Long-Term Pulmonary Arterial Hypertension Disease Management (REVEAL)." *Circulation* 2010; 122:164-72). Unfortunately, the mortality rate on the waiting list for patients with iPAH is high, between 20% and 30% (see Dandel M, et al. "Survival of patients with idiopathic pulmonary arterial hypertension after listing for transplantation: impact of iloprost and bosentan treatment." *J. Heart Lung Transplant*, 2007; 26:898-906). Approximately 20% of the patients listed for lung transplantation in the United States still die on the waiting list within 1 year after being listed (see Chen H, et al. "Impact of the lung allocation score on lung transplantation for pulmonary arterial hypertension." *Am J Respir Crit Care Med*, 2009; 180:468-74).

During the past several years, a number of transplant programs have introduced extracorporeal life support (ECLS) devices as part of their armamentarium to bridge patients on the waiting list to lung transplantation (BTT) (see Mangi A A, et al. "Bridge to lung transplantation using short-term ambulatory extracorporeal membrane oxygenation" *J. Thorac. Cardiovasc. Surg.*, 2010, 140:713-5 and Garcia J P, et al. "Ambulatory extracorporeal membrane oxygenation: a new approach for bridge-to-lung transplantation." *J. Thorac. Cardiovasc. Surg.*, 2010; 139: e137-9 and Fadel E, et al. "Long-term outcome of double lung and heart-lung transplantation for pulmonary hypertension: a comparative retrospective study of 219 patients." *Eur. J. Cardiothorac Surg.* 2010; 38:277-84). One option is a low-resistance oxygenator designed for pulsatile blood flow driven by the patient's cardiac output. It was originally designed as a pumpless device connected between the femoral artery and the femoral vein and was used in a variety of clinical situations, such as chest trauma, adult respiratory distress syndrome, pneumonia, and airway obstruction (see Fischer S, et al. "Bridge to lung transplantation with the extracorporeal membrane ventilator Novalung in the venovenous mode: the initial Hannover experience." *ASAIO J*, 2007; 53:168-70 and Hoeper M M, and Welte T. "Extracorporeal lung assist: more than kicking a dead horse?" *Eur. Respir. J.*, 2008, 32:1431-2).

A low-resistance oxygenator was used for the first time as a BTT for patients with hypercapnic respiratory failure by the group in Hannover (see Fischer S, Simon A R, Welte T, et al. Bridge to lung transplantation with the novel pumpless interventional lung assist device NovaLung." *J. Thorac. Cardiovasc Surg.*, 2006, 131:719-23). Others have also demonstrated that this low-resistance membrane provides a unique option for patients with pulmonary hypertension by interposing the device between the pulmonary artery (PA)

and the left atrium (LA), thereby resulting in an oxygenated right-to-left shunt and reducing RV afterload (see Strueber M, Hoeper M M, Fischer S, et al. Bridge to thoracic organ transplantation in patients with pulmonary arterial hypertension using a pumpless lung assist device. *Am J Transplant*, 2009, 9:853-7 and Schmid C, Philipp A, Hilker M, et al. Bridge to lung transplantation through a pulmonary artery to left atrial oxygenator circuit. *Ann Thorac Surg.*, 2008, 85:1202-5).

Up to now the PA-LA system was always inserted in the operating room with open chest surgery. The femoral vein and artery were first dissected and exposed under local anesthesia because of the high risk of hemodynamic collapse with induction of general anesthesia. Patients were then placed on VA-ECMO through the femoral vessels, anesthetized, and intubated. Once stable on VA-ECMO, a sternotomy was performed, a right-angled cannula was placed into the LA through the right superior pulmonary vein, and a straight cannula was placed into the main PA. The pumpless $CO_2$ removal device was connected and VA-ECMO was weaned. The sternotomy was closed in a standard fashion, the femoral cannulas were removed, the femoral vessels repaired, and the groin was closed. The cannulas were removed from the PA and LA at the time of transplant.

Disadvantages of this surgical PA-LA ECLS are the need for general anesthesia, additionally temporary VA-ECMO during implantation and a median sternotomy for device implantation. That makes this option a very last resort. Para-corporeal $CO_2$ removal instituted trough median sternotomy provide sufficient $CO_2$ removal, but the complexity of open chest surgery with central cannulation and post-implantation management limits their widespread adoption.

Extracorporeal support (ECS) configurations for $CO_2$ removal as arterial femoral—venous femoral cannulation resolve symptoms. But the key disadvantage of the AV approach is the need for arterial vessel cannulation with the potential side effects of arterial injury and limb ischemia. Additionally the both cannulas in the leg vessels limit ambulation.

Limited potential for ambulation prevents patients from participating in rehabilitate therapies, which in recent years have shown to be highly beneficial for extracorporeal life support. ECLA with a pump remains a highly specialized form of treatment with many possible complications, an inherent problem of significant blood traumatization and clotting disturbances. These and other disadvantages present in the devices and methods of the prior art are addressed by the dual lumen cannula system of the present invention.

SUMMARY OF THE INVENTION

The invention relates to the field of medical devices and their use. More specifically, the invention relates to the design and use of a multi or dual cannula assembly, which is configured for percutaneous application. By establishing percutaneously a shunt with a dual lumen cannula between PA and LA it is possible to use the PA-LA pressure gradient as the driving force for the blood flow through the drainage lumen out of the body and back into the body through the delivery lumen. Thereby it is possible to attach a blood $CO_2$ removal device and/or oxygenator device and return blood with lowered $CO_2$ concentration and/or increased $O_2$ concentration into the vascular system of a patient in need thereof. The assemblies of the present invention provide inter alia the following advantages:

(i) since no wearable pump is required $CO_2$ removal can be effected without providing a pump or an energy source for the pump. This in turn allows mobilization, (earlier) hospital discharge and faster recovery of the patients;

(ii) there are no objects (e.g. valves or impellers) in the blood flow path, which results in less blood cell damage;

(iii) the jugular vein as access point results in a very short circuit (tip to tip of the cannula may be less than 100 cm) with a minimized blood to tubing surface contact area which leads to a lower anti-coagulation regime; and (iv) the design also eliminates the need for a heater.

In the following text, selected aspects are described, where, aside from these aspects, the present disclosure may contain further advantageous aspects, which address one, some, or all of the problems or have one, some, or all of the advantages stated above. Thus, the following description should not be construed as limiting or restricting the disclosure of the application.

In the independent claims, but not necessarily restricted thereto, particularly advantageous subject-matter is defined. Further advantageous embodiments are subject of the dependent claims but not necessarily restricted thereto. Particularly, the following description such as the description of the drawings or the one exemplary embodiments may also contain advantageous features.

The present invention, according to a first aspect, relates to a multi or dual lumen cannula assembly comprising:
(i) a proximal part comprising two separate tubes: a first tube defining a blood delivery lumen and second tube defining a blood drainage lumen,
(ii) a mid-portion comprising the two tubes integrated into one, preferably cylindrical, body up to a bifurcation in which the first tube and the second tube separate into a first and second distal tube; and
(iii) a distal part comprising the two separate distal tubes.

In a second aspect the present invention relates to a blood decarboxylation assembly comprising:
(i) the multi or dual lumen cannula assembly of the present invention; and
(ii) a blood $CO_2$ removal device attached to the first and second tube of the proximal part, e.g. the proximal ends of the first and second tube, of said multi or dual lumen cannula assembly in such a way that the $CO_2$ concentration of blood flowing through the second tube into the blood $CO_2$ removal device is lowered when passing through the blood $CO_2$ removal device and into the first tube.

In a third aspect the present invention relates to a method of treating a patient with lung and/or heart disease, wherein at least the distal and middle part or mid-portion of the multi or dual lumen cannula assembly of the invention are inserted into the body of the patient.

In a fourth aspect the present invention relates to a method of treating a patient with lung and/or heart disease including the step of:
(i) inserting two single lumen cannula from the right jugular vein and placing the distal tip of one the cannula's in LA and the distal tip of the other cannula in PA; inserting two single lumen cannula from the left jugular vein;
(ii) inserting two single lumen cannula, wherein the first is inserted from the right jugular vein and the second from the femoral vein and placing the distal tip of the first cannula in LA and the distal tip of the second cannula in PA;

(iii) inserting two single lumen cannula, wherein the first is inserted from the left jugular vein and the second from the femoral vein and placing the distal tip of the first cannula in LA and the distal tip of the second cannula in PA.

In a further aspect the present invention relates to a blood treatment or blood processing assembly or system, particularly a blood decarboxylation assembly and/or a blood oxygenation assembly, which comprises the multi or dual lumen cannula assembly as described further above or below, and one of, an arbitrarily selected plurality of, or all of the following elements:

- a blood decarboxylation device, e.g. a pECLA $CO_2$ removal device,
- a blood oxygenation device, e.g. an oxygenator,
- a pump, particularly an extra-corporeal pump,
- an electronic control unit,
- a valve or a valve-type member, and
- an ECG (electrocardiogram) device, e.g. for recording and/or monitoring the ECG of a patient.

BRIEF DESCRIPTION OF THE DRAWINGS

In the drawings, identical elements, identically acting elements and elements of the same kind may be provided with the same reference numerals in different figures.

Figure 1:
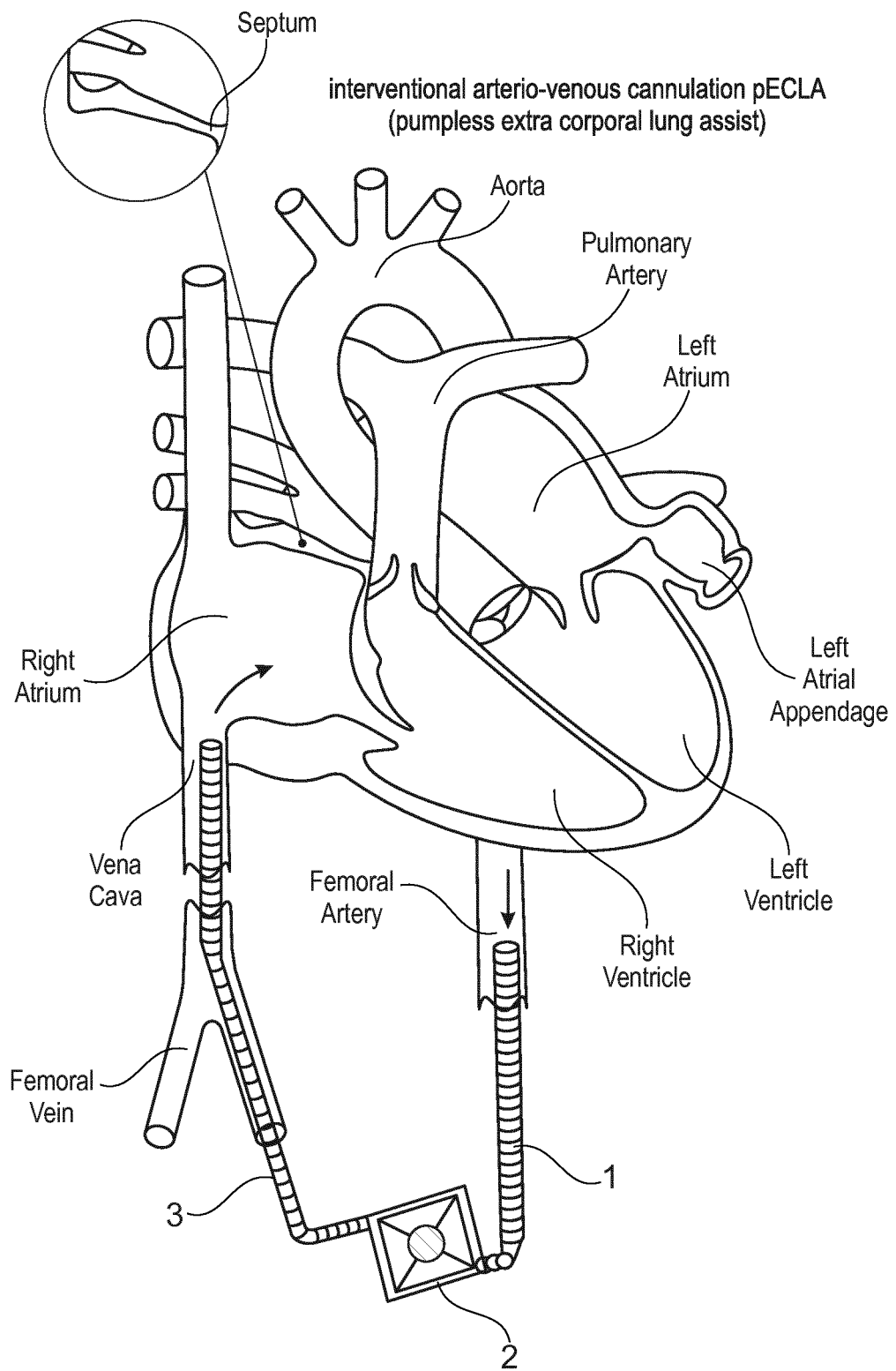
FIG. 1 Shows a prior art arrangement for extracorporeal $CO_2$ removal termed "interventional arterio-venous cannulation pECLA (pumpless extra corporal lung assist)". In this arrangement blood flows through the tip of a first single lumen cannula (outflow cannula 1), inserted into the leg artery (femoral artery) of a patient with the tip of the cannula being positioned in the aorta of the abdomen to an extracorporeal lung assist device (pECLA $CO_2$ removal device 2) comprising a membrane for $CO_2$ removal, which is positioned between the legs of the patient and the blood is redelivered through the tip of a second single lumen cannula (inflow cannula 3) inserted into the leg vein (femoral vein) with the tip of the cannula being positioned in the vena cava. The pressure difference between the aorta and the vein is sufficient to overcome the resistance of the inlet of the first single lumen cannula, the membrane of the $CO_2$ removal device and the outlet of the second single lumen cannula. A disadvantage of this prior art method is that the patient has to stay immobile.
Figure 2:
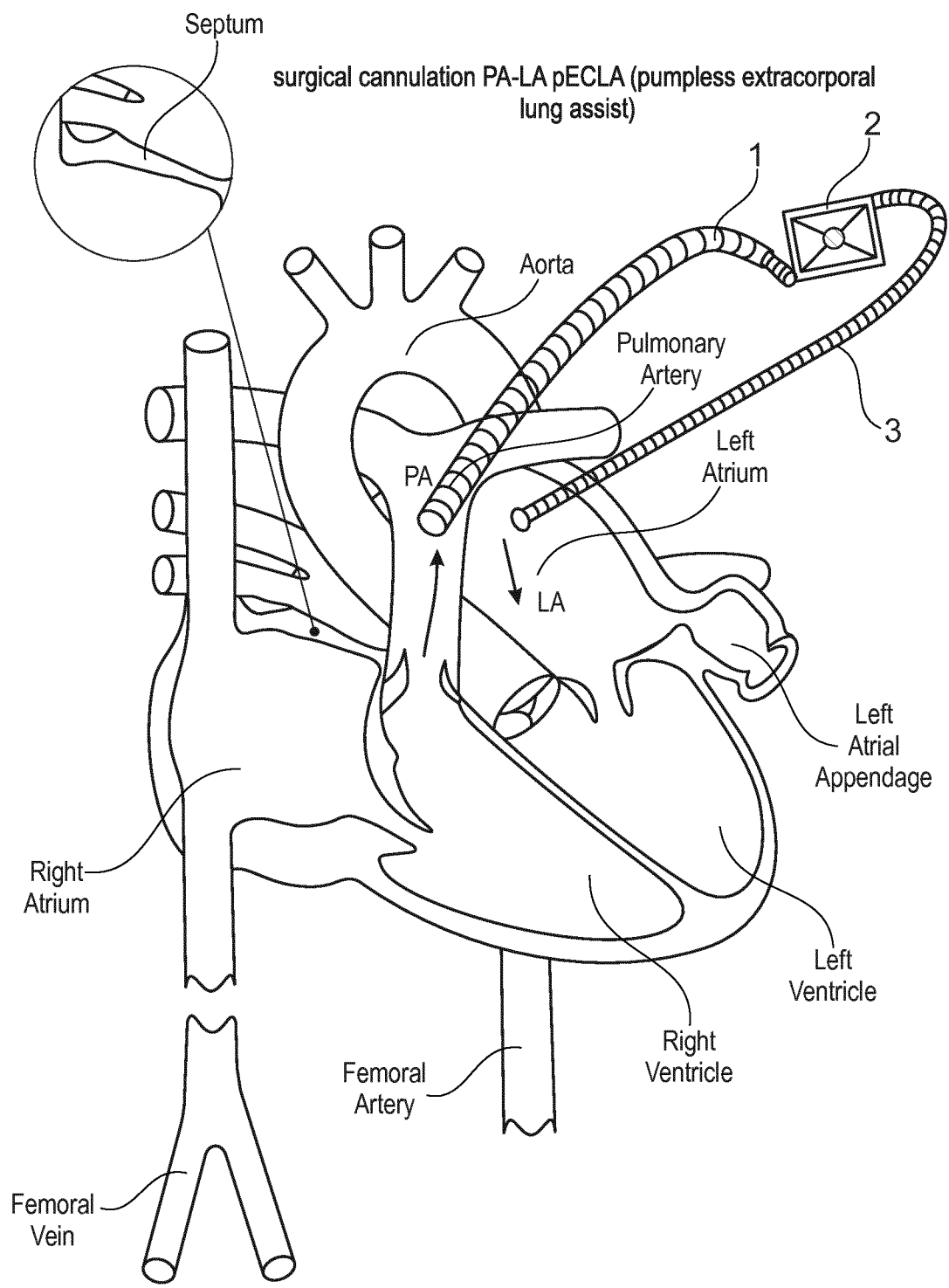
FIG. 2 Shows a prior art arrangement for extracorporeal $CO_2$ removal termed "Surgical cannulation PA-LA pECLA (pumpless extracorporal lung assist)". In this arrangement the thorax of the patient is opened, a first single lumen cannula (outflow cannula 1) is affixed (usually by sewing) to the pulmonary artery (PA) and a second single lumen cannula (inflow cannula 3) is affixed (usually by sewing) to the left atrium (LA). There is an increased pressure in patients with pulmonary hypertension, which drives the blood through the first single lumen cannula, to an extracorporeal lung assist device (pECLA $CO_2$ removal device 2) comprising a membrane for $CO_2$ removal, through the membrane of the $CO_2$ removal device and out of the second single lumen cannula back into the LA without requiring a pump. A disadvantage of this prior art prior art method is the high complication rate associated with the opening of the thorax of the patient.

In the drawings, the following references are used:
1 outflow cannula
2 $CO_2$ removal device
3 inflow cannula
4 dual lumen cannula
41 proximal part
42 mid-portion 43 distal part
5 first tube
51 first distal tube
6 second tube
61 second distal tube
62 opening
7 introducer
8 introducer
9 wire
10 wire
11 third tube
111 third distal tube
12 bifurcation
13 bifurcation
14 oxygenation device
15 pump
16 electronic control unit
17 first valve
18 second valve
19 tube
20 guide tube
21 guide tube
22 cuff
23 balloon
24 ECG device It will be appreciated that the embodiments depicted in the drawings can be modified easily, e.g to include other features—either as substitutes or additional features—described herein above and below, even if not shown in or explained explicitly in conjunction with one of the drawings. The modifications form, of course, part of the present disclosure.

DETAILED DESCRIPTION OF PREFERRED EMBODIMENTS

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In a first aspect the present invention relates to a multi or dual lumen cannula assembly comprising:
(i) a proximal part comprising two separate tubes: a first tube defining a blood delivery lumen and second tube defining a blood drainage lumen,
(ii) a mid-portion comprising the two tubes integrated into one, preferably cylindrical, body up to a bifurcation in which the first tube and the second tube separate into a first and second distal tube; and
(iii) a distal part comprising the two separate distal tubes.

It is preferred that the first distal tube is configured to reach the left atrium (LA) once inserted trans-septally into the body of a patient. To that end the first distal tube has a length of at least 4 cm. The length of the first and second distal tube is determined in the context of the present invention from the bifurcation in the middle part of the cannula. It is further preferred that the second distal tube is configured to reach the left pulmonary artery (PA) once inserted into the body of a patient. To that end the second distal tube has a length of at least 10 cm.

In a preferred embodiment the ratio of the length of the first distal tube and or to the length of the second distal tube is between 0.4 to 0.8. This ratio reflects the length of the first distal tube that is required to be inserted trans-septally into the LA and for the distal tip of the second distal tube to be positioned in the PA, preferably closely behind the heart valve. Based on the size of the heart different absolute lengths of the first and second distal tube may be required to optimally position the two tubes in two different patients. However, the ratio of distances will be similar for different patients, e.g. for toddlers and adults.

In a preferred embodiment the length of the first distal tube is at least 4 cm shorter than the length of the second distal tube. Again this relative length difference reflects the final positions at which the tip of the first and second distal tubes will be positioned once inserted into the body of a patient.

In a preferred embodiment:
(i) the length of the first distal tube is in the range of 4 to 40 cm, preferably 6 to 30 cm, more preferably 8 to 20 cm and the length of the second distal tube is in the range of 10 to 50 cm, preferably 12 to 40 cm, more preferably 14 to 35 cm and even more preferably 16 to 30 cm; and/or
(ii) the outer diameter of the first distal tube is in the range of 2.6 mm to 10.33 mm, preferably between 3 and 9 mm, more preferably 4 to 8 mm and the diameter of the second distal tube is in the range of 3.33 mm to 11 mm, preferably 4 to 10.5 mm and more preferably 4.5 to 10.0 mm. The diameter of the cannulas are chosen in each case in such that the respectively desired amount of blood, e.g. between 0.5 to 5 l/min, can flow through the cannula out of and back into the body of the patient without being exposed to shear forces but also to prevent interference with the blood flow through the vasculature in general.

In a preferred embodiment the length of the second distal tube is adjustable. Adjustability may be achieved by using an insertable tube, e.g. the second tube is movable within the middle part of the cannula and preferably also within the proximal part, if the two tubes are integrated in the proximal part into one cylindrical body. This is preferred, if one type of dual lumen cannula is used for patients with differently sized hearts.

In a preferred embodiment the length of the first distal tube and/or of the second distal tube is fixed.

In a preferred embodiment the second distal tube is configured to drain liquid simultaneously from two or more areas of the heart and its vasculature, preferably through the distal end, preferably the distal tip of the second distal tube and/or through one or more holes or openings along the side of the second distal tube. The distal end may comprise an opening at the tip of the distal end and/or several openings around the circumference of the end of the distal tube, e.g. within an area of 1 to 3 cm of the distal tip. Such an area is also called for the purpose of this application a "section of openings". The further opening(s) or section of openings along the side of the second distal tube are located in such that they will be positioned in a certain region of the heart and its vasculature once the second distal tube is inserted and has reached its final position within the heart and heart vasculature (see FIGS. 4 and 5). These one or more further openings or sections of openings, preferably two further openings or sections of openings are preferably distributed around the circumference of the second distal tube and may be distributed over a stretch of 0.5 to 5 cm, preferably 1 to 3 cm. The size of the openings will be determined by the outer diameter of the distal tube. Typically the diameter of the openings is less than 1/10 of the outer diameter of the distal tube in the area in which the openings are located.

It is preferred that the second distal tube is configured to drain liquid simultaneously from:
(i) PA and right ventricle (RV); in this case the distance of the one or more openings or sections of openings from the tip of the second distal tube is in the range of 3 cm to 15 cm, preferably 5 to 20 cm;
(ii) PA, RV and right atrium (RA); in this case the distance of the one or more openings or sections of openings, preferably two further openings or sections of openings from the tip of the second distal tube is in the range of 6 cm to 35 cm, preferably 8 to 20 cm. It is preferred that the first further openings or section of openings is positioned 3 to 15 cm away from the opening and/or section of openings at the tip of the second distal tube and that the second further openings or section of openings are positioned 3 to 10 cm away from the first further openings or section of openings;
(iii) PA, RV, RA and superior vena cava (SVC); in this case the distance of the one or more openings or sections of openings from the tip of the second distal tube is in the range of 10 cm to 35 cm;
(iv) RV; in this case the distance of the one or more openings or sections of openings from the tip of the second distal tube is in the range of 3 cm to 35 cm;
(v) RA; in this case the distance of the one or more openings or sections of openings from the tip of the second distal tube is in the range of 6 cm to 35 cm; or
(vi) SVC; in this case the distance of the one or more openings or sections of openings from the tip of the second distal tube is in the range of 10 cm to 35 cm.

In an embodiment, the second distal tube is configured to drain liquid from one, e.g. only from one, of the following parts or areas, simultaneously from an arbitrarily selected plurality of the following parts or areas or simultaneously from all of the following parts or areas of the heart and its associated vasculature: PA, RV, RA, SVC. The tip of the second distal tube and/or openings in the second distal tube may be arranged in the respective desired part or area.

Figure 3:
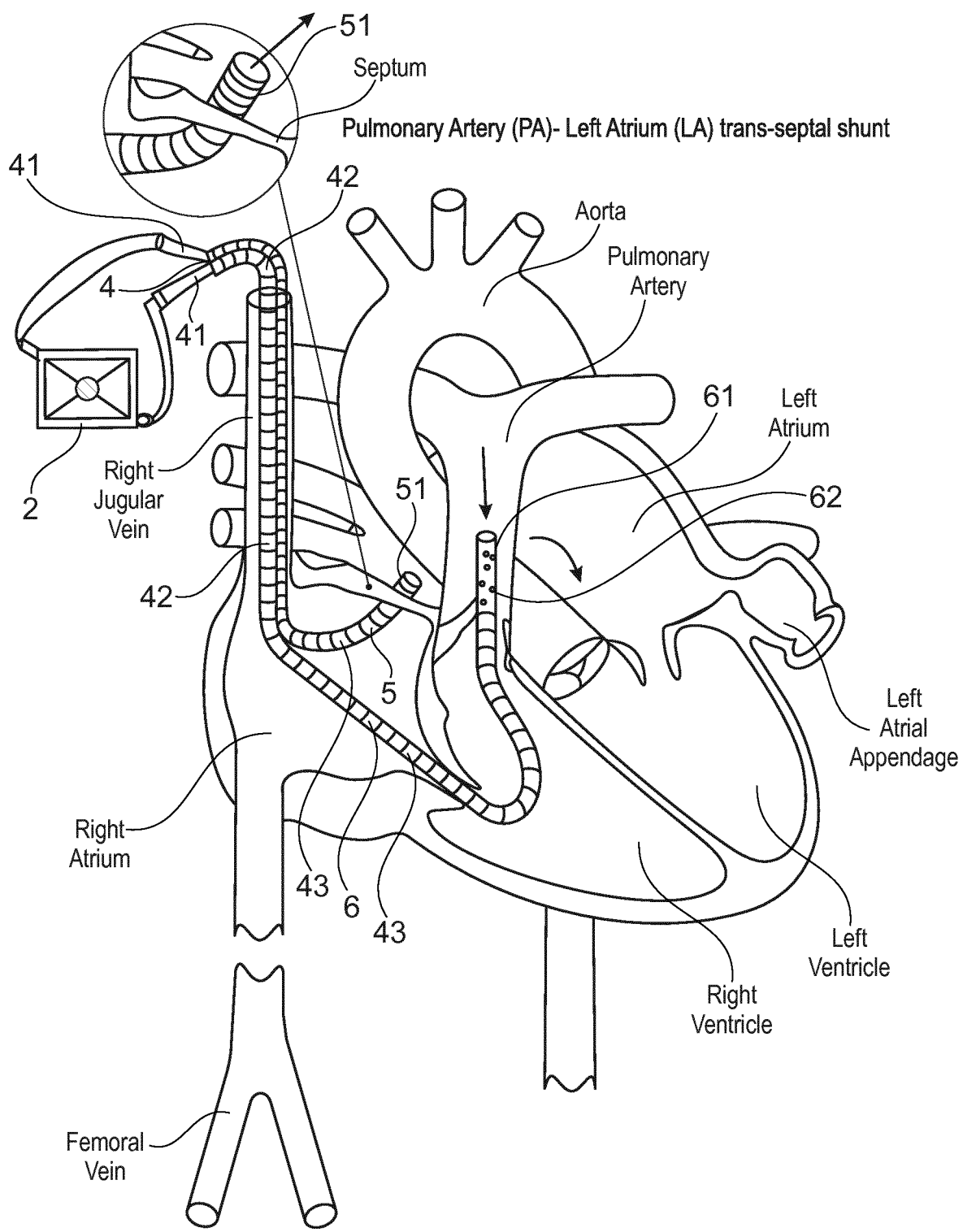
FIG. 3 Shows a preferred embodiment of the dual lumen cannula 4 of the present invention and its position within the body of a patient during treatment, which is termed "Pulmonary Artery (PA)—Left Atrium (LA) trans-septal shunt". The dual lumen cannula comprises a first tube 5 and a second tube 6. In a proximal part 41 of the dual lumen cannula 4, the two tubes 5, 6 are separate. In a mid-portion 42 of the dual lumen cannula 4, the two tubes 5 and 6 are connected with each other, preferably integrated in a single, e.g. cylindrical body. In a distal part 43 the cannula 4 the two tubes 5, 7 are separated after a bifurcation and the cannula comprises two separate distal tubes, a first distal tube 51 and a second distal tube 61, in the distal part 43. In this arrangement the dual lumen cannula of the present invention is inserted with the distal part 43 first percutaneously into the right jugular vein. One distal part comprising the second tube (second distal tube 61) is inserted through the right atrium (RA), through the right ventricle (RV), through the semilunar valves into the pulmonary artery (PA) in such that the tip of this distal part is located in the PA. The distal part comprising the first tube (first distal tube 51) is inserted trans-septally from the right atrium into the left atrium (LA) in such that the tip of this distal part is located in the LA. In hypertonic patients the pressure difference between the LA and the PA is sufficient to drive the blood from the PA, to an extracorporeal lung assist device comprising a membrane for $CO_2$ removal, through the membrane of the $CO_2$ removal device and out into the LA without requiring a pump. The relatively slow flow (between 0.5 to 1.5 L/min) is sufficient for $CO_2$ removal. Optionally, the intake of blood can be improved by providing additional openings 62 around the circumference of the distal end of the second distal tube 61 forming a section of openings at the tip of the second distal tube. In a preferred embodiment, the blood is also oxygenated (the oxygenator is not explicitly illustrated). In this embodiment a pump (likewise not illustrated) is used to overcome the resistance of the oxygenator. Preferably, the pump is a pulsating pump or driven in a pulsed manner, such as by an electronic control unit (likewise not illustrated) which may be provided. The pulsed operation may be controlled according to the beats of the heart which is monitored or was recorded by an ECG device. The associated data—either pre-recorded or monitored—may be stored in or, e.g. continuously, transmitted to the control unit. If the ECG device monitors the heart activity the ECG device is expediently connected to the control unit. It should be readily apparent that the first distal tube 51, instead of ending in the LA as illustrated, could also end in the LV or the Aorta ascendens.
Figure 4:
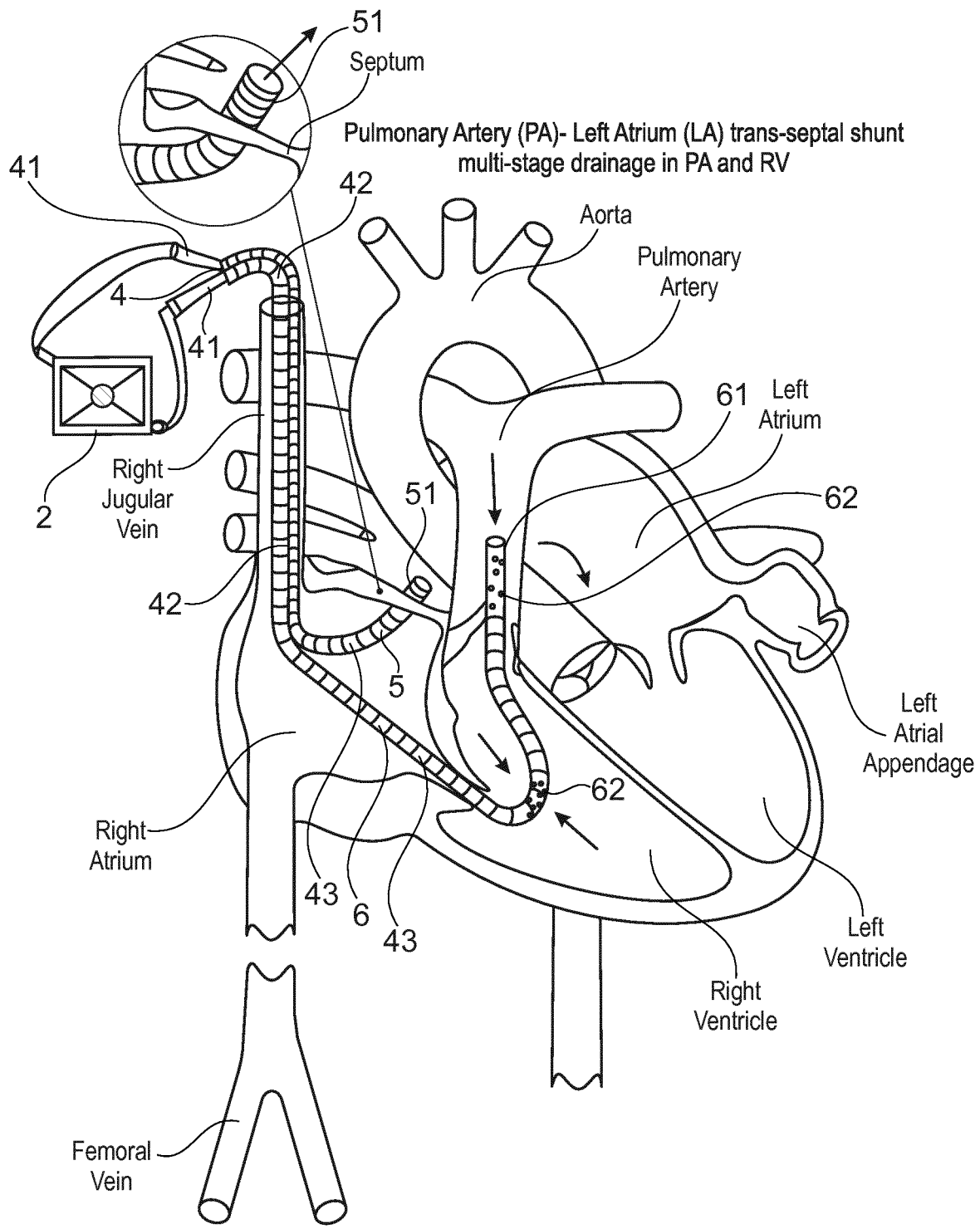
FIG. 4 Shows a preferred embodiment of the dual lumen cannula of the present invention termed "Pulmonary Artery (PA)—Left Atrium (LA) trans-septal shunt multi-stage drainage in PA and RV". In this embodiment the second distal tube 61 which drains blood from the body of the patient is configured to have one or more openings or sections of openings 62 at two positions along the second distal tube 61. The first opening is at the tip of the second distal tube. Optionally, the intake of blood can be improved by providing additional openings around the circumference of the distal end of the second distal tube forming a section of openings at the tip of the second distal tube. The distal tube comprises further openings or a further section of openings 62, typically over a length of 0.5 to 5 cm that is(are) positioned between 3 to 15 cm, e.g. 6 to 8 cm, apart from the first opening or section of openings 62. The openings or sections of openings 62 are positioned in such distance that the openings are located in the respectively desired area of the heart and heart vasculature. In the embodiment shown in FIG. 4 the sections of openings are positioned in such a distance of each other that upon insertion of the cannula one section of openings is positioned in the PA and the other section is positioned in the RV.
Figure 5:
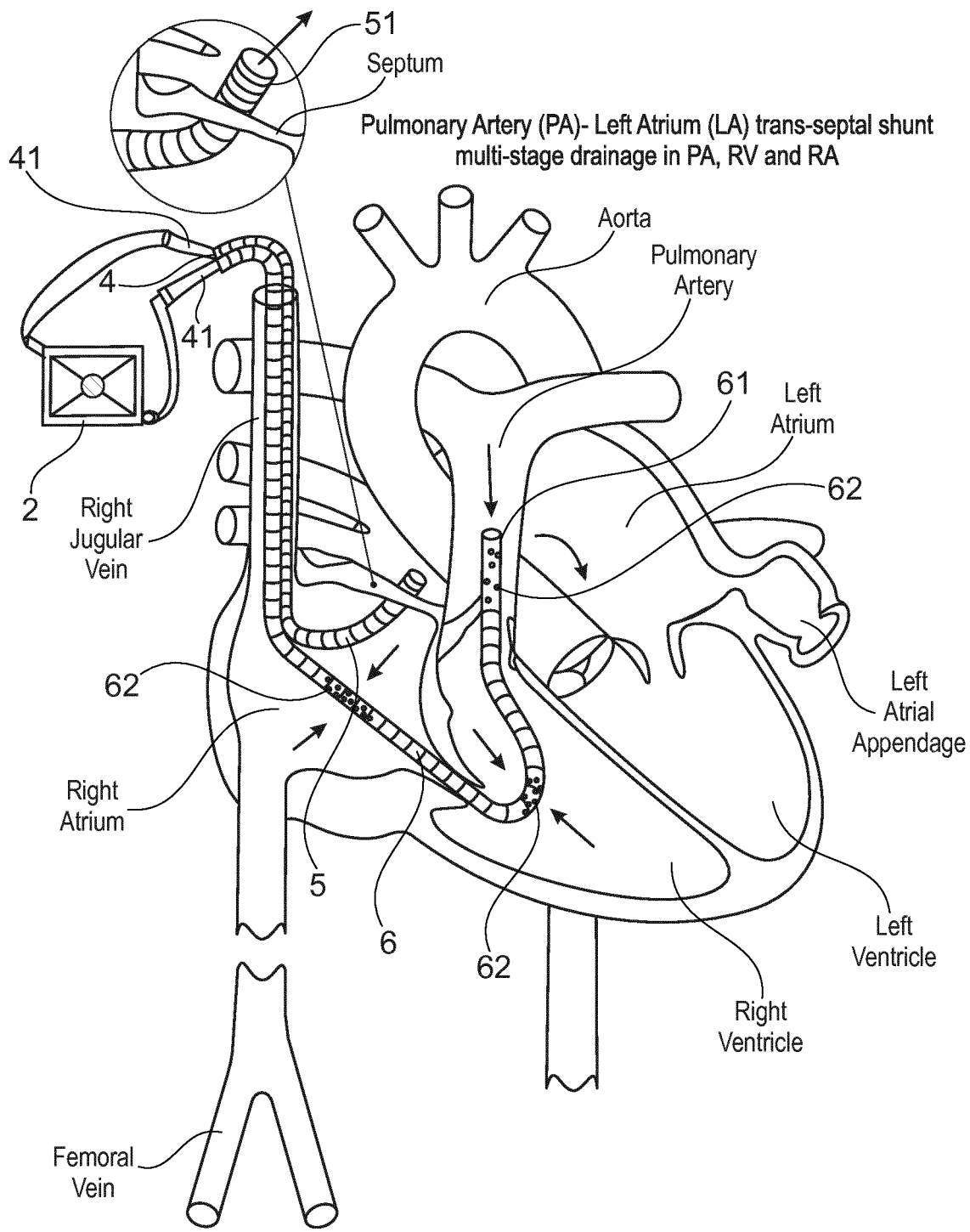
FIG. 5 Shows a preferred embodiment of the dual lumen cannula of the present invention termed "Pulmonary Artery (PA)—Left Atrium (LA) trans-septal shunt multi-stage drainage in PA, RV and RA". In this embodiment, the second distal tube 61 that drains blood from the body of the patient is configured to have one or more openings or sections of openings 62 at three positions along the second distal tube. The first opening 62 is at the tip of the second distal tube. Optionally, the intake of blood can be improved by providing additional openings around the circumference of the distal end of the second distal tube 61 forming a section of openings 62 at the tip of the second distal tube. The distal tube comprises further openings or a section of openings 62 in a second area, typically over a length of 0.5 to 5 cm that is(are) positioned between 3 to 15 cm, e.g. 6 to 8 cm, apart from the first opening or section of openings 62 and in a third area, typically over a length of 0.5 to 5 cm that is(are) positioned between 3 to 10 cm, e.g. 6 to 8 cm, apart from the second opening or section of openings 62. The three separate openings or sections of openings 62 are positioned in such distance that the openings are located in the respectively desired area, expediently different areas, of the heart and the heart vasculature. In the embodiment shown in FIG. 5 the sections of openings are positioned in such a distance of each other that upon insertion of the cannula the first section of openings 62 is positioned in the PA, the second is positioned in the RV and the third in the right atrium (RA).
Figure 6:
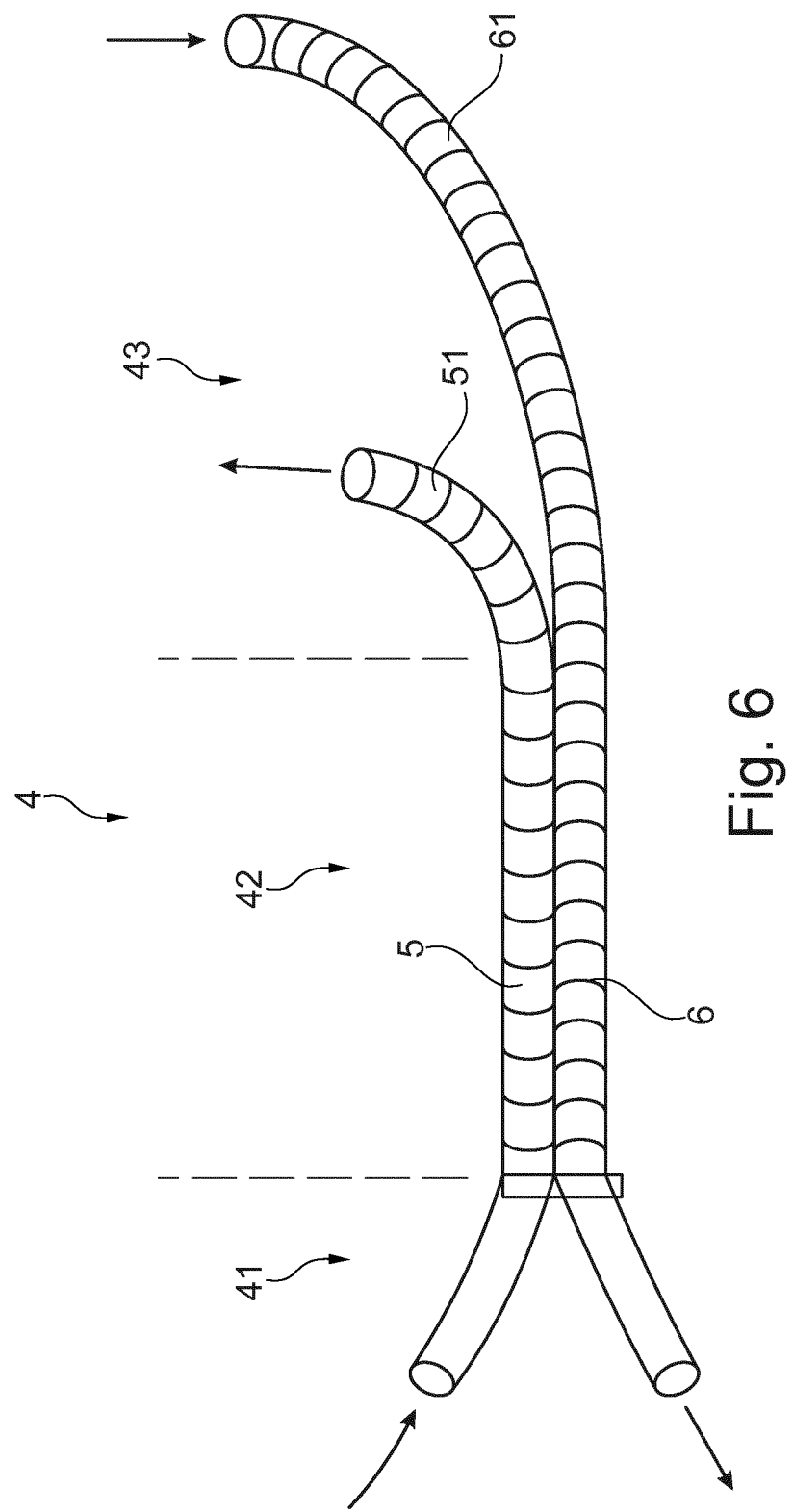
FIG. 6 Shows a preferred embodiment of the dual lumen cannula of the present invention with proximal (41), mid (42) and distal part (43). In this arrangement the dual lumen cannula of the present invention features two separate tubes behind a bifurcation at the distal part, which can be placed in different chambers of the heart and in arteries or veins.
Figure 7:
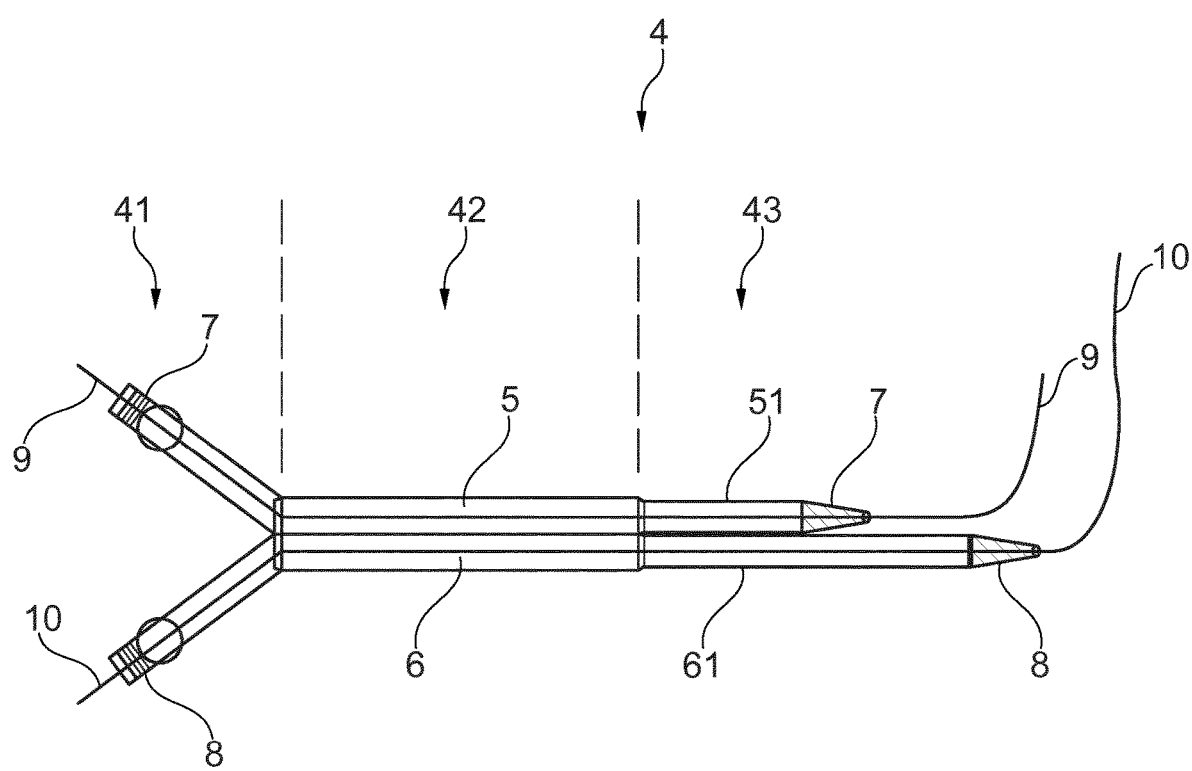
FIG. 7 Shows a preferred embodiment of the dual lumen cannula 4 of the present invention in the delivery mode, e.g. as delivered by the manufacturer and/or ready to be inserted into the body, with two separate introducers (introducer first tubing 7, introducer second tubing 8) and two separate guide wires (wire first tubing 9, wire second tubing 10) in the second lumen. The respective wire 9, 10 reinforces the associated tube 5, 6 and/or extends over the entire associated tube. The respective introducer preferably extends over the entire associated tube. After insertion of the cannula 4 into the body, the respective introducer and/or the respective wire may be removed. The guide wires may be used to move the distal tubes 51 and 61 independently from one another. In this way, the distal tubes may be guided to the desired part or area of the heart.
Figure 8:
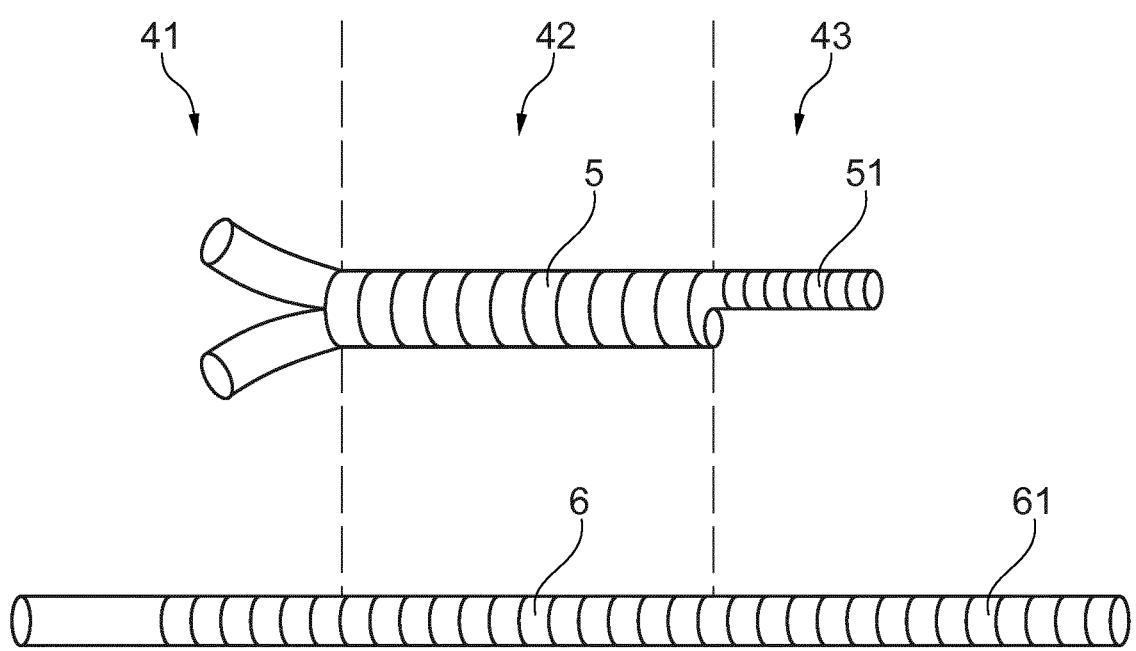
FIG. 8 Shows a preferred embodiment of the dual lumen cannula of the present invention with a diameter increase at the mid part (42) of the first tube 5 of at least 50%. So that the second tube 6 can be inserted into the first tube and the distal part of the second tube is adjustable in lengths for optimal placement.
Figure 9:
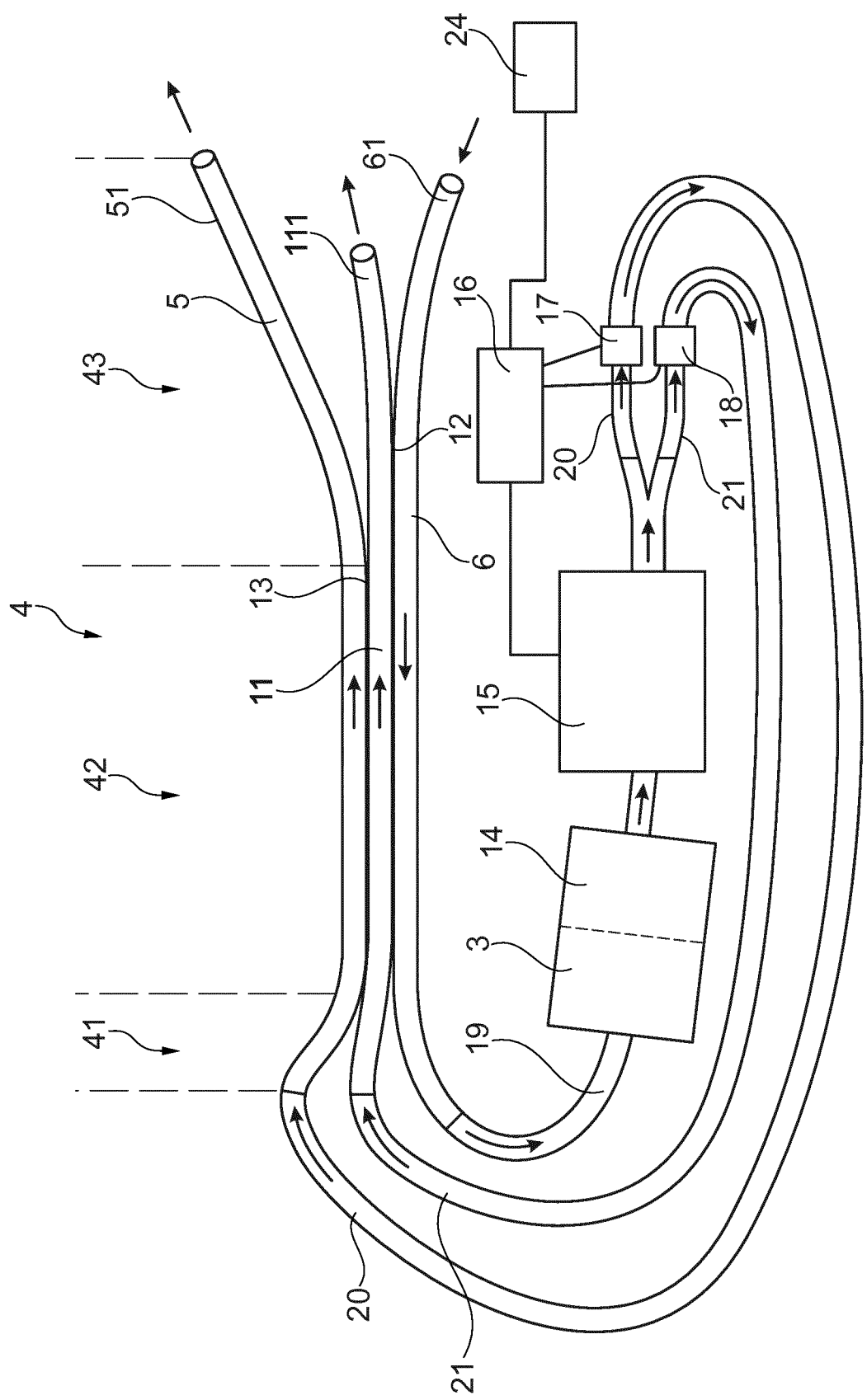
FIG. 9 Shows a preferred embodiment of the invention, e.g. a blood treatment or processing assembly, such as a decarboxylation assembly. The decarboxylation assembly comprises the cannula assembly 4, which is, essentially, configured as described further above. The cannula assembly comprises in the depicted embodiment a third tube 11 in addition to the first and second tubes 5, 6, where the third tube likewise defines a blood delivery lumen as the first tube but is configured to be placed with its tip in the other half of the heart or its associated vasculature, e.g. in the RA or the RV, as compared to the first tube 5. Consequently, the blood delivery lumen of the cannula assembly 4 is distributed over two sub-lumen. In the mid portion 42 the three tubes are integrated in a common, e.g. cylindrical, body. In the proximal part 41 the three tubes may already be separated as illustrated or integrated into a body. In the distal part 43, the three tubes are separate. Specifically, the third tube 11 separates in a bifurcation 12 from the second tube 6 to form a third distal tube 111, where this bifurcation 12 is depicted as distally offset from the bifurcation 13 where the first tube 5 separates from the other two tubes 11, 6. However, the bifurcations 12, 13 may coincide as seen axially along the cannula assembly or the bifurcation 12 may be arranged proximally offset from the bifurcation 13. In use, blood can be delivered into different halves of the heart or its associated vasculature through the third distal tube 111 and the first distal tube 51 and the second tube 6 is configured to drain blood (as indicated by the arrows). The second and third tubes are arranged to end in the right half of the heart or heart vasculature, either in the same area (e.g. RA, LA, or PA) or in different areas (e.g. PA and LA). The first tube 51 is configured to pass through the septum from the right into the left half of the heart as explained above already. Of course, if no delivery into the right half of the heart is desired, the third tube may be dispensed with. In addition to the cannula assembly 4, the decarboxylation assembly comprises the blood decarboxylation device 3, an oxygenation device 14, a pump 15, an electronic control unit 16, e.g. a PC, a first valve 17, a second valve 18, and an ECG (electrocardiogram) device 24. From the proximal end of the second tube 6, blood flows to the devices 3, 14 via a tube and is decarboxylated and oxygenated in the respective device, where the blood drainage and/or the blood delivery is preferably driven by the pump 15. The stream of processed blood is then divided into two streams, one stream being guided into the first tube 6 and the other stream being guided into the third tube 11 of the cannula assembly 4, via associated guide tubes 20, 21, respectively. Alternatively, the division into two streams may occur before the blood is treated—decarboxylzed or oxygenized—where only one of the blood streams is treated and the other stream is not. This is not explicitly illustrated. In this case, the third tube may be configured to deliver non-treated blood, whereas the first tube may be configured to deliver treated blood. The valves 17 and 18 can be opened and closed independently to selectively adjust the proportion of blood for the respective stream delivered to the different halves of the heart. The electronic control unit 16 controls operation of the pump 15 and/or of the valves 17, 18, e.g. to achieve a pulsative flow of the blood which is delivered to the heart or heart vasculature and/or based on data fed to the control unit by the ECG device 24.
Figure 10:
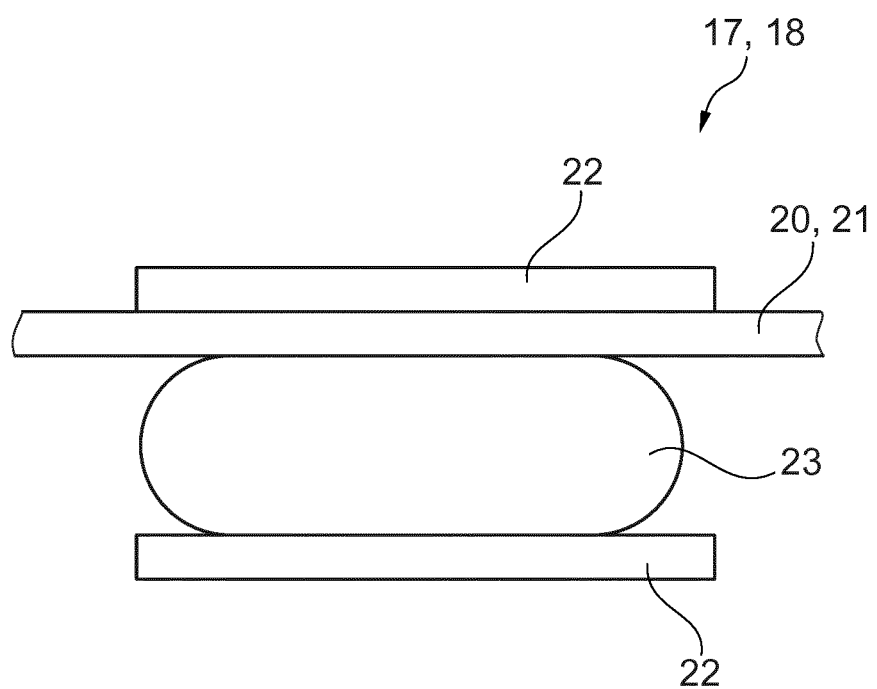
FIG. 10 Shows an embodiment of the valve (17 or 18) described previously. The respective guide tube 20, 21 is, in a section, retained within a rigid cuff 22, e.g. from metal. An inflatable and deflatable balloon 23, e.g. a balloon catheter, (a gas inlet for inflating is not shown explicitly) is also retained in the cuff 22. When the balloon is inflated, the tube is squeezed, as the rigid cuff does not deform under the pressure transferred to it by the balloon, and the flow rate through the associated tube reduces until it stops entirely. When the balloon is deflated, the flow rate is increased again.

As is apparent from FIGS. 3 to 5 the two distal tubes will be inserted in different locations of the heart and heart vasculature of the patient. To allow the targeted insertion the first distal tube and/or the second distal tube comprises in a preferred embodiment an introducer each with at least a single guide wire lumen of at least 0.356 mm, preferably at least 0.457 mm or at least 0.889 mm.

In an embodiment, the first distal tube is configured to deliver liquid to one of the following parts or areas of the heart and its associated vasculature, e.g. only to one of the parts or areas: LA, LV, Aorta, preferably the Aorta ascendens. The tip of the first distal tube and/or openings of the first distal tube may be arranged in the respective desired part or area.

The dual lumen cannula of the invention is inserted through one access point, e.g. the jugular vein. In order to use the pressure differential between the systemic circulation and the pulmonary circulation the first distal tube is positioned in the LA and the second distal tube is positioned in the PA with optional additional openings or sections of openings in the RV, and RA. The trans-septal placement of the first distal tube is, thus a hallmark of the method of the present invention. The first distal tube is configured to facilitate the puncturing of the septum and insertion of the tube. Furthermore the first distal tube is configured to prevent blood drainage through the trans-septal opening once placed in the body. Furthermore the first distal tube is configured to prevent movement of the first distal tube once inserted through the opening in the septum. It is, thus preferred that the first distal tube comprises a trans-septal fixation. Such fixation is positioned close to the distal tip of the first distal tube, e.g. within 1 to 3 cm of the distal tip.

Blood cells are negatively affected by excessive shear forces. It is, thus preferred that the first and second tube are designed to reduce or essentially avoid shear forces. Accordingly, the first tube in a preferred embodiments comprises in its lumen a structure, preferably a helical structure, which creates a spiral outflow of liquids passed through said structure towards the distal end of the first distal tube. Similarly the second tube comprises in a preferred embodiment in its lumen a structure, preferably a helical structure, which creates a spiral inflow of liquids passed through said structure towards the proximal end.

In a preferred embodiment the first distal tube comprises at its distal end at least two suture lines. These suture lines are preferably configured to close the trans-septal puncture side after removal of the first distal tube. The suture lines comprise preferably at least 2 fingers in 180° direction each.

One advantage provided by the cannula of the present invention is that a pump is not required to pass the blood of the patient through the $CO_2$ removal device. The pressure difference resulting from the placement of the respective tips of the first and second distal tube is sufficient to provide blood flow in the range of 0.5 to 1.5 l/min. However, in some embodiments a higher blood flow than naturally provided by this arrangement may be desired. In this instances the cannula may be connected with a para-corporeal pump, preferably a membrane pump.

In a preferred embodiment the first distal tube is configured to reach the left ventricle (LV). To that end the first distal tube preferably has a length of at least 8 cm, preferably of between 8 to 15 cm.

In an alternative preferred embodiment the first distal tube has a length of at least 18 cm, preferably of between 18 to 30 cm. In this embodiment the distal tip of first distal tube is inserted through the aortic valve and placed in the Aorta ascendens. Accordingly, in this embodiment the trans-septal fixation is positioned at a greater distance from the distal tip in such that the distal tip is positioned in the Aorta ascendens once the first distal tube is affixed to the septum.

In a preferred embodiment the first and/or second tube is wire re-inforced. This facilitates insertion of the assembly into the body and placement of the respective tube at a desired location.

The distal tubes and the mid portion of the dual channel or lumen cannula of the present invention are configured to be inserted into the body. Accordingly, the surface of the distal tubes and the middle part is biocompatible and smooth to be inserted into the vasculature and to stay in the vasculature for a prolonged period of time. The length of the middle part is such that the bifurcation can be positioned in the right ventricle after insertion into the body. Thus, the length of the middle part is preferably in the range of 15 to 40 cm, preferably 20 to 35 cm.

The combined length of the distal part and the middle part (as measured from the tip of the longer of the two distal tubes) is preferably between 35 to 80 cm, more preferably 40 to 60 cm. The relatively short length of the cannula is a further advantage of the cannula of the present invention.

The proximal part of the dual channel or lumen cannula is typically not inserted into the body and, thus n a preferred embodiment the proximal part is configured to be positioned outside the body of the patient. In particular in long term applications it is preferable that the proximal part is puncture proof, abrasion resistant, and/or kink resistant. To that end the proximal part may be provided with additional coating and/or a fabric cover.

It is also preferred that the proximal part comprises the two tubes integrated into one cylindrical body and/or comprises a bifurcation in which the first tube and the second tube separate into a first and second proximal tube. Such separate tubes may by attached to the respective inlet and outlet ports of a $CO_2$ removal and/or other devices.

It should be appreciated that, in the present disclosure, the first distal tube does not have to but, of course, may be configured such that it ends in the LA—i.e. the tip may be arranged in the LA. Rather, it may end in other areas of the heart or/and its associated vasculature such as in the LV or in the Aorta, particularly in the Aorta ascendens. Alternatively or additionally it should be appreciated that the second distal tube does not have to but, of course, may be configured such that it ends in the PA—i.e. the tip may be arranged in the PA. Rather, it may end in other areas of the heart and its associated vasculature such as in the RV or/and in the RA.

Generally, if the first and/or second distal tube passes through a particular part or/and area of the heart in its entirety (e.g. RA, RV, LA, LV) and ends in another part or/and area of the heart or in the adjoining vasculature (e.g. PA or Aorta Ascendens), that part of the heart is relieved as it has to provide less pump power as it is bridged or bypassed by the cannula assembly.

In an embodiment, the first and second distal tube do have different lengths. Particularly, after the bifurcation in which the first and second tub separate the lengths may be different. The first distal tube may be shorter than the second distal tube or vice versa. The length difference may be greater than or equal to one of the following values: 3 cm, 4 cm, 5 cm, 8 cm, 10 cm. Alternatively or additionally, the length difference may be less than or equal to: 35 cm, 30 cm, 20 cm, 15 cm, 12 cm, 11 cm.

In an embodiment, the first and second distal tubes are configured to be guided through and/or end in different halves of the human heart. The first distal tube is preferably configured to end in the left half of the heart (LV or LA)—or its associated vasculature, e.g. in the Aorta ascendens—and, particularly preferably, to pass from the right half through the septum which separates the two halves of the heart into the left half of the heart. The second distal tube is preferably configured to end in the right half of the heart (RV or RA)—or its associated vasculature, e.g. in the PA.

In an embodiment, the mid-portion and the distal part are configured to be inserted into the body, e.g. via the right jugular vein. The bifurcation is expediently arranged to be positioned in the right half of the heart, e.g. the RA. Consequently, the mid-portion may have a length, which is at least as great as the distance from the point of entry into the body to the right half of the heart, e.g. the RA. In the desired location in the right half of the heart, the tubes are separated and can be guided to the desired destination in different halves of the heart.

In an embodiment, the first tube defines only a first blood delivery sub-lumen, where the assembly comprises a further tube, e.g. a third tube, which defines a second blood delivery sub-lumen, where the blood delivery lumen comprises both, the first blood delivery sub-lumen and the second blood delivery sub-lumen. Thus, in other words, the blood delivery lumen of the assembly, instead of being defined by only one tube, may be defined, formed by, or distributed over a plurality of tubes, e.g. two tubes. Two different tubes defining different blood delivery sub-lumen may be configured to end in different halves of the heart. The first tube, e.g. the first distal tube, may be configured to end in the left half of the heart (e.g. in the LA or LV) or its associated vasculature like the Aorta, particularly the Aorta ascendens, whereas the third tube, e.g. a third distal tube, may end in the right half of the heart (e.g. in the RV or RV). In this way, blood—expediently treated blood, e.g. decarboxylzed ($CO_2$ has been removed) and/or oxygenized (oxygen has been added) blood, and/or non-treated blood—can be delivered to different segments of the heart, e.g. simultaneously or alternatingly. The ratio between blood delivered to the right half and the left half of the heart may be adjusted in this way. This may assist in weaning the patient from the treatment. Thus, depending on the condition of the patient, the heart may be stressed more or less, depending on into which heart half the greater proportion of blood is delivered. For weaning purposes, it is preferred that non-treated blood is delivered to the right heart or/and heart vasculature and treated blood is delivered to the left heart or/and heart vasculature.

The third tube may be part of the dual lumen assembly. In the proximal part, the third tube may be a separate tube or integrated with one or more of the first and second tube. In the mid-portion, the third tube may be integrated into the body together with the first and second tubes. The third tube may separate from the first and/or second tube at a bifurcation and form a third distal tube. This bifurcation may be the same bifurcation in which the first and second tubes separate or an additional bifurcation. The additional bifurcation may be arranged proximally or distally with respect to the bifurcation. In the additional bifurcation, the second and third tube may separate to form separate second and third distal tubes. Thus, the distal part of the cannula assembly may comprise three separate distal tubes.

In this embodiment, a separate, e.g. extracorporeal, pump connected to the assembly is particularly advantageous in order to provide the required pump power as the heart on its own may not have enough power. Alternatively or additionally, a blood oxygenation device may be provided which is connected to the assembly.

In an embodiment, the third distal tube is configured to deliver liquid to one of the following parts or areas of the heart and its associated vasculature: PA, RV, RA, SVC. The tip of the third distal tube and/or openings in the third distal tube may be arranged in the respective desired part or area.

In an embodiment, the tip of the third distal tube and the tip of the second distal tube are configured to be arranged in different areas or in the same area of the right half of the heart or its associated vasculature.

In an embodiment, the first blood delivery sub-lumen and the second blood delivery sub-lumen are different. In other words, the first and third tubes may have different diameters. The diameter of the third tube may be less than the one of the first tube, e.g. by 50% or more. Thus, the main delivery lumen may be the one defined by the first tube, which can be assisted by blood delivered through the third tube.

In an embodiment, the first blood delivery sub-lumen and the second blood delivery sub-lumen are equal.

In an embodiment, as seen along the cannula assembly, the distal tips of the second and third tubes are arranged offset from one another. The length of the respective tube—second or third tube—between the bifurcation where the second and third tubes separate and the distal tip of this tube may be different for the second and third tubes. This ensures that, even if the tips are placed in the same area of the heart, e.g. in the RA, the blood delivery does not interfere too much with the blood drainage.

In an embodiment, the distal tip of the first distal tube is or is configured to be arranged distally from the aortic valve, e.g. in the Aorta ascendens. The first distal tube may be secured to the Aorta ascendens. Specifically, the tip may be fixed to the Aorta to be arranged centrally within the Aorta. The LV may be stressed less in this way, as the blood is fed to the Aorta, bypassing the LV. The distal tip of the cannula is self-centering with an expanded cylindrical nitinol mesh design. By removing the cannula the cylindrical nitinol mesh is collapsing.

In this embodiment, a separate, e.g. extra-corporeal, pump connected to the assembly is particularly advantageous in order to provide the required pump power. Alternatively or additionally, a blood oxygenation device may be provided which is connected to the assembly.

In an embodiment, the first distal tube comprises a transseptal fixation, preferably one wire mesh disk at the LA site, or two wire mesh disks, a first one at the LA site and a second one at the RA site of the septum.

A further aspect of the present invention relates to a blood treatment or blood processing assembly or system, particularly a blood decarboxylation assembly and/or a blood oxygenation assembly, which comprises the multi or dual lumen cannula assembly as described further above or below, and one of, an arbitrarily selected plurality of, or all of the following elements:
- a blood decarboxylation device, e.g. a pECLA $CO_2$ removal device,
- a blood oxygenation device, e.g. an oxygenator,
- a pump, particularly an extra-corporeal pump,
- an electronic control unit,
- a valve or a valve-type member, and
- an ECG (electrocardiogram) device, e.g. for recording and/or monitoring the ECG of a patient.

In an embodiment, the assembly is pumpless.

In an embodiment, the electronic control unit is configured to control operation of the pump. The pump may drive drainage and/or delivery of blood through the cannula assembly.

In an embodiment, the electronic control unit is configured to operate the pump based on data, preferably currently monitored data, retrieved from the ECG device.

In an embodiment, the treatment assembly is configured for a pulsed delivery of blood through the blood delivery lumen. Thus, the blood delivery may be pulsative. This, as opposed to a constant or essentially constant blood flow rate, may achieve a flow rate, which changes with time, e.g. periodically. A pulsed flow may reduce the risk of formation of thrombus, as the blood flow is likely less laminar and more turbulent. The risk of a formation of a thrombus is particularly high when the flow is laminar. The assembly is preferably configured such that the pulsed delivery of the blood is controlled by data retrieved from an ECG device, preferably current data, when the ECG monitors the heart activity, or stored data when the ECG device is not or not continuously connected to the control unit.

In an embodiment, the pump is operated or controlled in a pulsed manner. Operation of the pump may be controlled by data retrieved from the ECG device, preferably current data, when the ECG monitors the heart activity, or stored data, when the ECG device is not or not continuously connected to the control unit.

In an embodiment, the delivery of blood, e.g. a pulsed delivery, may be controlled by the valve or valve-type member. The member may be arranged and configured to selectively reduce or close the blood deliver lumen and, thereafter, to increase or open the blood delivery lumen. The valve may cooperate with the tube which defines a blood delivery lumen, e.g. the first or third tube, on an outer surface of the associated tube, particularly in the proximal part of the cannula assembly or a tubing connected thereto. The valve may be designed as a squeeze valve configured to squeeze the respective tube to reduce or close the blood delivery lumen. Operation of the valve may be controlled manually and/or by the electronic control unit. If a third tube which defines a blood delivery sub lumen is provided in addition to the first tube, the valve may cooperate with the first tube or the third tube. Another valve may be provided to cooperate with the other one of the first and third tubes. The valves interacting with the first and third tube are, preferably, operable independently from one another, such that it can be controlled how much blood is delivered into which half of the heart independently. The valves interacting with the first and third tube are operable to control the ratio of the flow rates of blood being delivered to the left half to blood being delivered to the right half. A pulsed or non-pulsed pump may be used in this context.

In an embodiment, the valve is formed by means of an inflatable balloon, which is e.g. provided by a balloon catheter, the balloon being operatively coupled to a tube forming part of the proximal part of the cannula assembly (e.g. first or third tube) or an additional tube being fluidly connected to a tube of the proximal part of the cannula assembly (e.g. first or third tube). The balloon and the tube may be surrounded by a rigid bearing surface, e.g. a cuff, such that inflating the balloon squeezes the tube, which may reduce the flow rate. If the tube is squeezed off, flow through the tube is prevented entirely. When the balloon is deflated, the flow rate may, again, be increased.

In a further aspect the present invention relates to a blood decarboxylation assembly comprising:
(i) the dual lumen cannula assembly of the present invention, and
(ii) a blood $CO_2$ removal device attached to the first and second tube of the proximal part of said dual lumen cannula assembly in such a way that the $CO_2$ concentration of blood flowing through the second tube into the blood $CO_2$ removal device is lowered when passing through the blood $CO_2$ removal device and into the first tube.

In a preferred embodiment the assembly according to the second aspect of the invention comprises no pump.

In a preferred embodiment the assembly comprises an extra-corporeal pump preferably a centrifugal pump or membrane pump.

In a preferred embodiment the blood decarboxylation assembly comprises in addition a blood oxygenation device.

In a third aspect the present invention relates to a method of treating a patient with lung and/or heart disease, wherein the distal and middle part of the dual lumen cannula assembly of the present invention is inserted into the body of the patient.

In a fourth aspect the present invention relates to a method of treating a patient with lung and/or heart disease including the step of:
- (i) inserting two single lumen cannula from the right jugular vein and placing the distal tip of one the cannula's in LA and the distal tip of the other cannula in PA;

inserting two single lumen cannula from the left jugular vein;
- (ii) inserting two single lumen cannula, wherein the first is inserted from the right jugular vein and the second from the femoral vein and placing the distal tip of the first cannula in LA and the distal tip of the second cannula in PA;
- (iii) inserting two single lumen cannula, wherein the first is inserted from the left jugular vein and the second from the femoral vein and placing the distal tip of the first cannula in LA and the distal tip of the second cannula in PA.

In a preferred embodiment of the method according to the third and fourth aspect of the present invention, the disease is selected from the group of Chronic Obstructive Pulmonary Disease (COPD), Acute Respiratory Distress Syndrome (ARDS), Pulmonary Arterial Hypertension (PAH), Right Ventricle Failure (RVF).

In a preferred embodiment of the method according to the third and fourth aspect of the invention no open chest surgery is used to insert the dual lumen cannula into the body of the patient.

In a preferred embodiment of the method according to the third and fourth aspect of the present invention the method includes the step of using the jugular vein as access point for the trans-septal puncture.

In a preferred embodiment of the method according to the third and fourth aspect of the present invention the method includes the step of using the jugular vein as access point.

In a preferred embodiment the method includes step of using the femoral vein as access point for trans-septal puncture. After the puncture the distal end of the wire may be placed in the LA. The other distal end of the guide wire from femoral access may be changed to jugular vein access with a special guide.

The percutaneous PA-LA approach is also pumpless and can be maintained for several weeks with minimal blood damage and remarkably low morbidity. If a membrane exchange is required a brief clamping and quick disconnecting and reconnecting of the inflow and outflow cannula has to be done to change the membrane device.

The percutaneous PA-LA cannulation with the jugular vein as access point constitutes the most physiological mode of support because it creates a very short low-resistance circuit in parallel with the right heart and improves RV function too, as a result of an immediate decrease in its afterload. It is a pumpless short circuit with a low priming volume and a low-resistance $CO_2$ removal device that offers the possibility of long-term use.

To place the trans-septal arm of the dual lumen cannula in the LA, a trans-septal puncture from RA to LA is needed. Trans-septal puncture equipment via the jugular vein access is limited and most physicians are not familiar with this access point. The available standard materials (needle, sheath, dilator, wires etc. angle and lengths) are configured for the trans-septal puncture via the femoral vein.

After the trans-septal puncture the distal coil end of the wire is placed in the LA. To maneuver the proximal end of the guide wire from the femoral access site to the jugular vein access a special guide wire with a minimum floppy part (proximal to the coil end) of 60 cm is needed. With this wire it is possible to perform a 180° U-turn and to re-enter with the proximal end the femoral sheath again and to push the wire through a guiding catheter so that it leaves the body through the sheath at the jugular vein.

The wire may be a super stiff wire with a coil end.

It is needless to say that features which are disclosed in conjunction with different aspects, examples or embodiments may be combined with one another. For example, features disclosed in conjunction with an assembly do also apply to a method and vice versa.

The invention claimed is:

1. A dual lumen cannula assembly comprising:
   - (i) a proximal part comprising two tubes: a first tube defining a blood delivery lumen and a second tube defining a blood drainage lumen,
   - (ii) a mid-portion comprising the two tubes integrated into one body up to a bifurcation in which the first tube and the second tube separate into a first and second distal tube; and
   - (iii) a distal part comprising the two separate distal tubes, wherein the first distal tube comprises a trans-septal fixation.

2. The dual lumen cannula assembly of claim 1, wherein the first distal tube has a length of at least 4 cm and the second distal tube has a length of at least 10 cm.

3. The dual lumen cannula assembly of claim 1, wherein the ratio of the length of the first distal tube and the length of the second distal tube is between 0.4 to 0.8.

4. The dual lumen cannula assembly of claim 1, wherein the length of the first distal tube is at least 6 cm shorter than the length of the second distal tube.

5. The dual lumen cannula assembly of claim 1, wherein:
   - (i) the length of the first distal tube is in the range of 4 to 40 cm and the length of the second distal tube is in the range of 10 to 50 cm; and/or
   - (ii) the outer diameter of the first distal tube is in the range of 2.6 mm to 10.33 mm and the diameter of the second distal tube is in the range of 3.33 mm to 11 mm.

6. The dual lumen cannula assembly of claim 1, wherein the length of the second distal tube is adjustable.

7. The dual lumen cannula assembly of claim 1, wherein the second distal tube is configured to drain liquid simultaneously from two or more areas of the heart and its vasculature.

8. The dual lumen cannula assembly of claim 1, wherein the second distal tube is configured to drain liquid simultaneously from:
   - (i) PA and right ventricle (RV) and the distance of the one or more openings or sections of openings from the tip of the second distal tube is in the range of 3 cm to 35 cm;
   - (ii) PA, RV and right atrium (RA) and the distance of the one or more openings or sections of openings from the tip of the second distal tube is in the range of 6 cm to 35 cm;

(iii) PA, RV, RA and superior vena cava (SVC) and the distance of the one or more openings or sections of openings from the tip of the second distal tube is in the range of 10 cm to 35 cm;
(iv) RV and the distance of the one or more openings or sections of openings from the tip of the second distal tube is in the range of 3 cm to 35 cm;
(v) RA and the distance of the one or more openings or sections of openings from the tip of the second distal tube is in the range of 6 cm to 35 cm; or
(vi) SVC and the distance of the one or more openings or sections of openings from the tip of the second distal tube is in the range of 10 cm to 35 cm.

9. The dual lumen cannula assembly of claim 1, wherein the first distal tube and/or the second distal tube comprise an introducer, wherein the respective introducer has at least a single guide wire lumen of at least 0.3556 mm.

10. The dual lumen cannula assembly of claim 1, wherein the trans-septal fixation comprises one wire mesh disk at the LA site or two wire mesh disks first at the LA site and second at the RA site.

11. The dual lumen cannula assembly of claim 1, wherein the first tube comprises in its lumen a helical structure, that creates a spiral outflow of liquids passed through said structure towards the distal end of the first distal tube.

12. The dual lumen cannula assembly of claim 1, wherein the second tube comprises in its lumen a helical structure, that creates a spiral inflow of liquids passed through said structure towards the proximal end.

13. The dual lumen cannula assembly of claim 1, wherein the cannula is connected with a para-corporeal membrane pump.

14. The dual lumen cannula assembly of claim 1, where the first distal tube has a length of at least 10 cm.

15. The dual lumen cannula assembly of claim 1, where the first distal tube has a length of at least 20 cm.

16. The dual lumen cannula assembly of claim 1, wherein the first and/or second tube is wire re-inforced.

17. The dual lumen cannula assembly of claim 1, wherein the proximal part:
(i) is configured to be positioned outside the body of the patient;
(iia) comprises the two tubes integrated into one cylindrical body; or
(iib) comprises a bifurcation in which the first tube and the second tube separate into a first and second proximal tube.

18. The dual lumen cannula assembly of claim 1, wherein the first tube defines only a blood delivery sub-lumen and the assembly comprises a third tube, which defines a blood delivery sub-lumen, where the first tube and the third tube are configured to be guided through and/or end in different halves of the heart.

19. A blood decarboxylation assembly comprising:
(i) the dual lumen cannula assembly of claim 1, and
(ii) a blood $CO_2$ removal device attached to the first and second tube of the proximal part of said dual lumen cannula assembly in such a way that the $CO_2$ concentration of blood flowing through the second tube into the blood $CO_2$ removal device is lowered when passing through the blood $CO_2$ removal device and into the first tube.

20. The blood decarboxylation assembly of claim 19, wherein the assembly comprises no pump.

21. The blood decarboxylation assembly of claim 19, wherein the assembly comprises an extra-corporeal pump.

22. The blood decarboxylation assembly of any of claim 19, further comprising one or more devices selected from the group consisting of a blood oxygenation device, a bubble trap, a flow sensor, a pressure sensor and tubing.

23. A method of treating a patient with lung and/or heart disease, wherein the distal and middle part of a dual lumen cannula assembly is inserted into the body of the patient, and wherein the dual lumen cannula assembly comprises:
(i) a proximal part comprising two tubes: a first tube defining a blood delivery lumen and a second tube defining a blood drainage lumen,
(ii) a mid-portion comprising the two tubes integrated into one body up to a bifurcation in which the first tube and the second tube separate into a first and second distal tube; and
(iii) a distal part comprising the two separate distal tubes, wherein the first distal tube comprises a trans-septal fixation.

\* \* \* \* \*

UNITED STATES PATENT AND TRADEMARK OFFICE
CERTIFICATE OF CORRECTION

Page 1 of 1

PATENT NO. : 11,400,197 B2
APPLICATION NO. : 16/097147
DATED : August 2, 2022
INVENTOR(S) : Heilmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 941 days.

Signed and Sealed this
Eleventh Day of February, 2025

Coke Morgan Stewart
*Acting Director of the United States Patent and Trademark Office*